(12) United States Patent
Nishimura

(10) Patent No.: US 10,544,857 B2
(45) Date of Patent: Jan. 28, 2020

(54) SENSOR AND GEAR DEVICE

(71) Applicant: NABTESCO CORPORATION, Tokyo (JP)

(72) Inventor: Takeshi Nishimura, Mie (JP)

(73) Assignee: NABTESCO CORPORATION, Tokyo (JP)

( * ) Notice: Subject to any disclaimer, the term of this patent is extended or adjusted under 35 U.S.C. 154(b) by 349 days.

(21) Appl. No.: 15/592,699

(22) Filed: May 11, 2017

(65) Prior Publication Data

US 2017/0335944 A1    Nov. 23, 2017

(30) Foreign Application Priority Data

May 20, 2016    (JP) ................... 2016-101204

(51) Int. Cl.
| | |
|---|---|
| *F16H 1/32* | (2006.01) |
| *F16H 57/04* | (2010.01) |
| *F16H 57/08* | (2006.01) |
| *G01N 33/28* | (2006.01) |

(52) U.S. Cl.
CPC .......... *F16H 57/0405* (2013.01); *F16H 1/32* (2013.01); *F16H 57/0404* (2013.01); *F16H 57/0486* (2013.01); *F16H 57/082* (2013.01); *G01N 33/2888* (2013.01); *F16H 2001/323* (2013.01)

(58) Field of Classification Search
CPC ... F16H 1/32; F16H 2001/323; F16H 57/0405
See application file for complete search history.

(56) References Cited

U.S. PATENT DOCUMENTS

| | | | | |
|---|---|---|---|---|
| 2,462,715 | A * | 2/1949 | Booth ....................... | H01F 7/02 200/61.09 |
| 3,317,042 | A * | 5/1967 | Botstiber ............. | B01D 29/118 210/86 |
| 3,432,750 | A * | 3/1969 | Botstiber ........... | G01N 15/0656 200/61.09 |
| 4,070,660 | A * | 1/1978 | Tauber ............... | G01N 33/2858 340/631 |
| 4,302,754 | A * | 11/1981 | Magee ............... | G01N 33/2858 340/631 |
| 4,598,280 | A * | 7/1986 | Bradford .................. | G07C 3/00 324/698 |
| 5,793,199 | A | 8/1998 | Kasahara et al. | |
| 6,679,801 | B2 * | 1/2004 | Nohara ..................... | F16H 1/32 184/6.12 |
| 9,218,693 | B2 * | 12/2015 | Hale ..................... | G07C 5/0825 |
| 9,724,995 | B2 * | 8/2017 | Ozaki ................... | B60L 3/0061 |
| 9,752,956 | B2 * | 9/2017 | McKimpson ....... | G01M 13/021 |
| 9,970,903 | B1 * | 5/2018 | Gerardi ................ | G01N 29/032 |

(Continued)

FOREIGN PATENT DOCUMENTS

| | | |
|---|---|---|
| JP | H10-078411 A | 3/1998 |
| JP | 2005-331324 A | 12/2005 |
| WO | WO-2016084595 A1 * 6/2016 ............... F16J 15/18 |  |

*Primary Examiner* — Sherry L Estremsky

(74) *Attorney, Agent, or Firm* — Pillsbury Winthrop Shaw Pittman, LLP

(57) ABSTRACT

The present application discloses a sensor provided with a detection portion that detects a foreign substance of a predetermined size or larger generated in a lubricant in a gear device and an output portion that, upon the detection portion detecting the foreign substance, outputs information indicating that the foreign substance has been detected.

9 Claims, 8 Drawing Sheets

(56) References Cited

U.S. PATENT DOCUMENTS

| | | | | |
|---|---|---|---|---|
| 10,107,135 B2* | 10/2018 | Schwarz | ............... | F01D 15/12 |
| 2017/0248572 A1* | 8/2017 | Byington | ............... | F16C 19/52 |
| 2017/0269036 A1* | 9/2017 | Foord | ............... | G01N 27/023 |
| 2017/0363529 A1* | 12/2017 | Ture | ............... | G01N 15/0656 |

* cited by examiner

SENSOR AND GEAR DEVICE

CROSS-REFERENCE TO RELATED APPLICATIONS

This application is based on and claims the benefit of priority from Japanese Patent Application Ser. No. 2016-101204 (filed on May 20, 2016), the contents of which are hereby incorporated by reference in their entirety.

TECHNICAL FIELD

The present invention relates to a technique of detecting an increase in risk of breakage of a gear device.

BACKGROUND

Various types of gear devices have been developed in various technical fields such as industrial robots, machine tools, and vehicles. A lubricant (lubricant oil) that reduces friction on a movable part of a gear device is important in prolonging life of the gear device. Japanese Patent Application Publication No. Hei 10-78411 and Japanese Patent Application Publication No. 2005-331324 propose techniques for examining quality of a lubricant. In the conventional examination techniques, a concentration of magnetic powder or an amount of metal powder in a lubricant is detected, and based on a result thereof, quality of the lubricant is evaluated. While being useful for evaluating deterioration in quality of a lubricant over a long period of time, these techniques are not suited for evaluating a malfunction risk of a gear device attributable to a sporadically caused malfunction factor.

SUMMARY

The present invention has as its object to provide a technique of detecting an increase in malfunction risk of a gear device attributable to a sporadically caused malfunction factor.

A sensor according to one aspect of the present invention is provided with a detection portion that detects a foreign substance of a predetermined size or larger generated in a lubricant in a gear device and an output portion that, upon the detection portion detecting the foreign substance, outputs information indicating that the foreign substance has been detected.

A gear device according to another aspect of the present invention is provided with an outer cylinder having an inner circumferential surface on which a plurality of internal teeth surrounding a predetermined output axis are formed, an oscillating gear meshed with the plurality of internal teeth, a crank shaft assembly that imparts oscillating rotation to the oscillating gear so that a center of the oscillating gear orbits about the output axis, a carrier that supports the crank shaft assembly and relatively rotates about the output axis with respect to the outer cylinder, and a sensor having a detection portion that detects a foreign substance of a predetermined size or larger floating in a lubricant in a detection space having a boundary at least partially formed by at least one of the outer cylinder and the carrier and an output portion that, upon the detection portion detecting the foreign substance, outputs information indicating that the foreign substance has been detected.

The above-mentioned technique is capable of detecting an increase in malfunction risk of a gear device attributable to a sporadically caused malfunction factor.

Objects, features, and advantages of the above-mentioned technique will become more apparent from the following detailed description and the appended drawings.

DESCRIPTION OF THE PREFERRED EMBODIMENTS

First Embodiment

Rubbing between movable parts (for example, rubbing between tooth surfaces) of a gear device may result in a gradual increase in amount of minute metal powder floating in a lubricant. Such an increase in amount of minute metal powder may gradually deteriorate lubrication performance of the lubricant. An increase in amount of minute metal powder, however, may be unlikely to lead to an instantaneous malfunction of the gear device. On the other hand, a large foreign substance (metal piece) peeled off from a movable part of the gear device may be likely to cause an instantaneous malfunction of the gear device. For example, when a large foreign substance bites in between movable parts of the gear device, in some cases, an excessive load may be applied to the movable parts of the gear device. A first embodiment describes a sensor capable of detecting a large foreign substance that is a possible cause of an instantaneous malfunction of the gear device.

Figure 1:
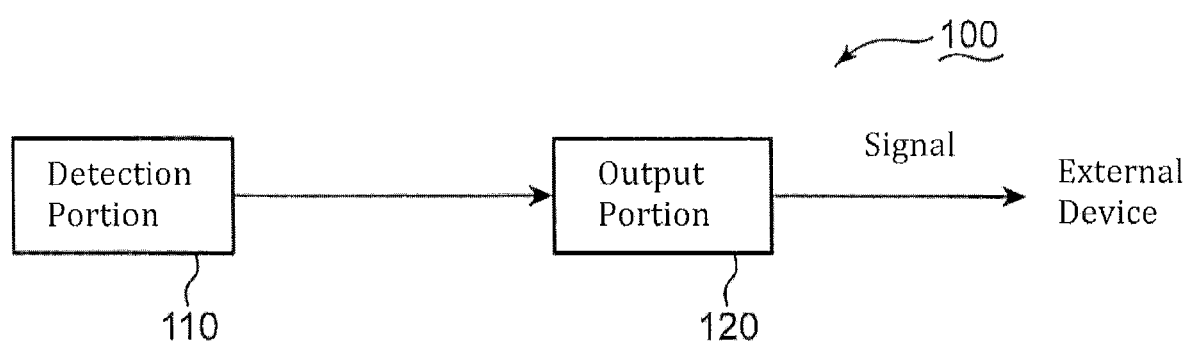
FIG. 1 is a schematic block diagram of a sensor of a first embodiment.

FIG. 1 is a schematic block diagram of a sensor 100 of the first embodiment. With reference to FIG. 1, a description is given of the sensor 100.

The sensor 100 may be provided with a detection portion 110 and an output portion 120. The detection portion 110 may detect a foreign substance of a predetermined size or larger generated in a lubricant (for example, lubricant oil) in a gear device (not shown). It may also be possible that the detection portion 110 has a mechanical structure formed to capture a foreign substance of a predetermined size or larger. Alternatively, it may also be possible that the detection portion 110 is a detection device that, based on an optical technique, an electromagnetic technique, and/or an acoustic technique, measures a particle diameter of a foreign substance in a lubricant. A principle of this embodiment may not be limited to a particular detection technique for detecting a foreign substance of a predetermined size or larger.

It may also be possible that a lower limit value of a size of a foreign substance to be detected by the detection portion 110 is determined so as to adapt to a structure and performance of a gear device in which the sensor 100 is mounted. In a case of a gear device having a robust structure, it may also be possible that a designer sets a lower limit value of a size of a foreign substance to be detected by the detection portion 110 to a large value. In a case of a gear device having a fragile structure, it may also be possible that a designer sets a lower limit value of a size of a foreign substance to be detected by the detection portion 110 to a small value.

Upon the detection portion 110 detecting a foreign substance, a detection result indicating that the foreign substance has been detected may be outputted from the detection portion 110 to the output portion 120. It may also be possible that the detection result is transmitted in the form of electric energy, outputted as an electric signal, or outputted as a wireless signal. The principle of this embodiment may not be limited to a particular information transmission technique for outputting a detection result from the detection portion 110 to the output portion 120.

Upon receipt of the detection result, the output portion 120 may generate a signal indicating that the foreign substance has been detected. The signal may be outputted from the output portion 120 to an external device (not shown). It may also be possible that the output portion 120 is a commonly used signal generation circuit or a commonly used output port that outputs electric energy. It may also be possible that the external device is a control device that controls a gear device, a warning device that, in accordance with a signal from the output portion 120, issues a warning sound or a warning message, or any other type of electric device. The principle of this embodiment may not be limited to a particular transmission destination of a signal outputted from the output portion 120.

Second Embodiment

Based on the design principle described in relation to the first embodiment, a designer can design various types of sensors. A sensor is sometimes disposed in a narrow space in a gear device and thus may preferably have a structure as simple as possible. A second embodiment describes a sensor having a simple structure.

Figure 2A:
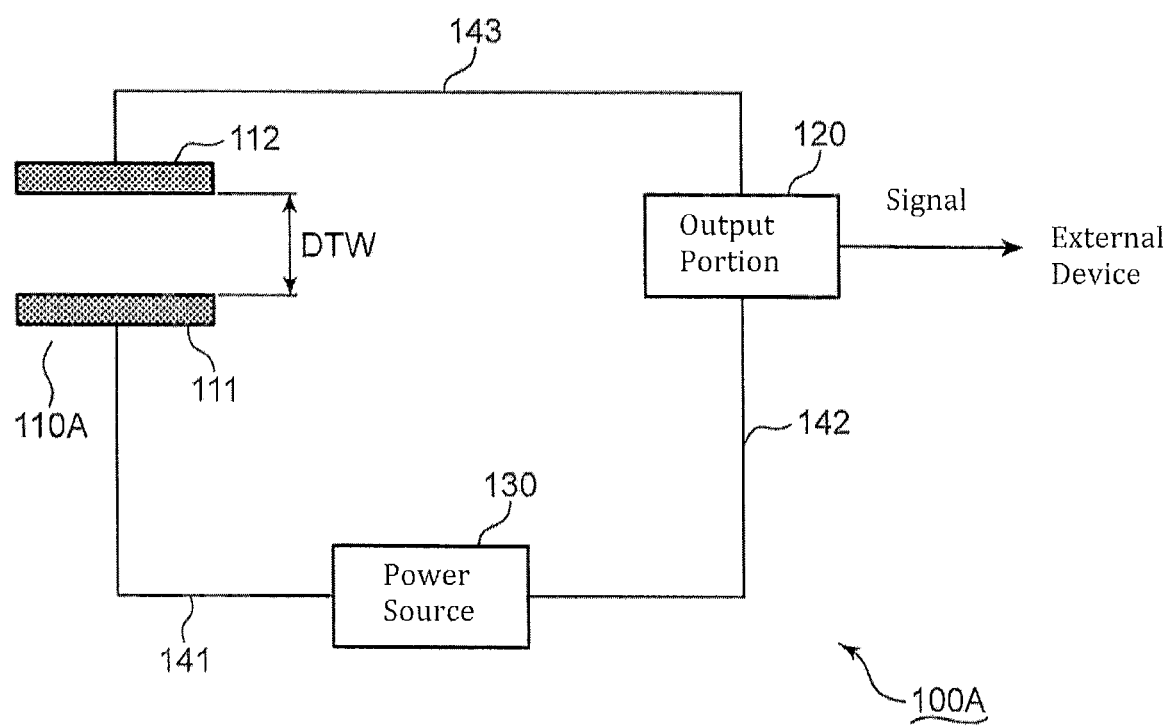
FIG. 2A is a conceptual diagram of a sensor of a second embodiment.
Figure 2B:
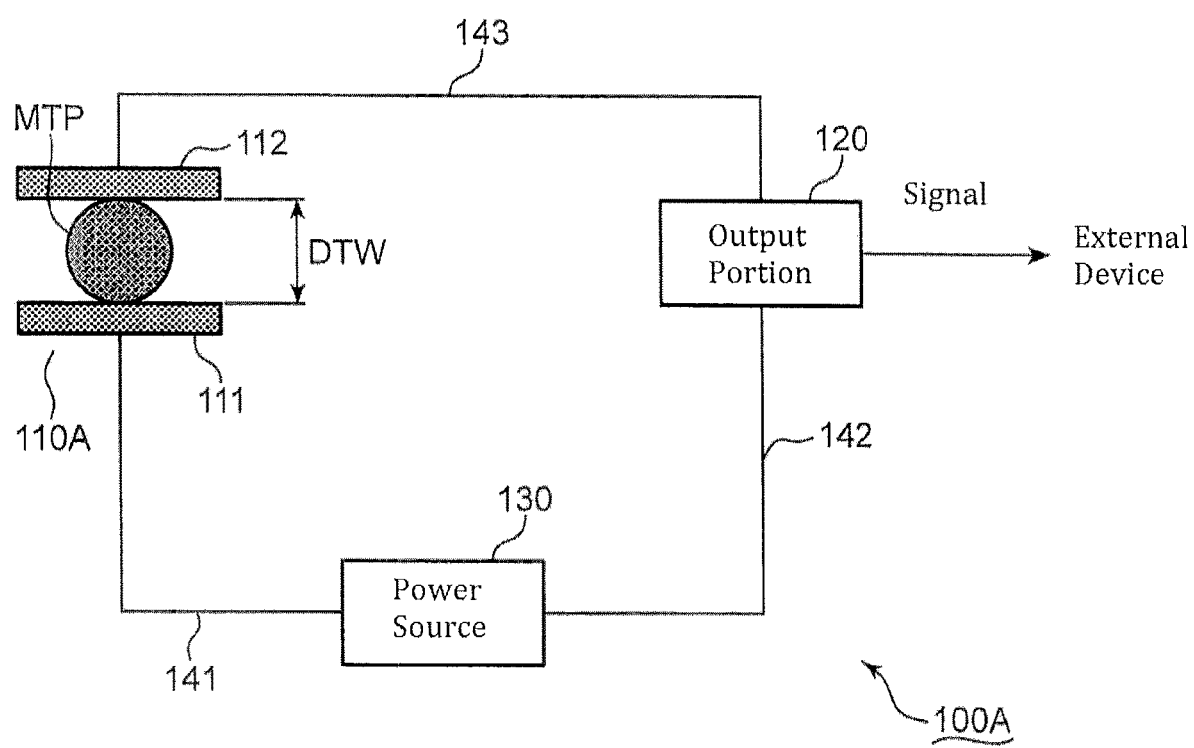
FIG. 2B is a conceptual diagram of the sensor of the second embodiment.

FIG. 2A and FIG. 2B are conceptual diagrams of a sensor 100A of the second embodiment. With reference to FIG. 2A and FIG. 2B, a description is given of the sensor 100A. The description of the first embodiment may be applied to elements denoted by the same reference characters as those in the first embodiment.

Similarly to the first embodiment, the sensor 100A may be provided with an output portion 120. The description of the first embodiment may be applied to the output portion 120.

The sensor 100A may be provided further with a detection portion 110A, a power source 130, a first line 141, a second line 142, and a third line 143. The detection portion 110A may include a first detection piece 111 and a second detection piece 112. It may also be possible that a width DTW of a gap between the first detection piece 111 and the second detection piece 112 is determined so as to adapt to a structure and performance of a gear device (not shown) in which the sensor 100A is mounted. In a case of a gear device having a robust structure, it may also be possible that a designer sets the width DTW to a large value. In a case of a gear device having a fragile structure, it may also be possible that a designer sets the width DTW to a small value.

As shown in FIG. 2B, a foreign substance MTP having a dimension not smaller than the width DTW may be held between the first detection piece 111 and the second detection piece 112. It may also be possible that the first detection piece 111 and the second detection piece 112 are a pair of metal plates disposed substantially parallel to each other. Alternatively, it may also be possible that each of the first detection piece 111 and the second detection piece 112 is an end surface of a conductive wire. A principle of this embodiment may not be limited to a particular structure of the first detection piece 111 and the second detection piece 112.

The first line 141 may electrically connect the power source 130 to the first detection piece 111. The second line 142 may electrically connect the power source 130 to the output portion 120. The third line 143 may electrically connect the output portion 120 to the second detection piece 112. As shown in FIG. 2A, in the absence of the foreign substance MTP, a circuit constituted of the detection portion 110A, the output portion 120, the power source 130, the first line 141, the second line 142, and the third line 143 may be disconnected between the first detection piece 111 and the second detection piece 112. At this time, electric power may not be supplied from the power source 130 to the output portion 120. On the other hand, since the foreign substance MTP generated from a gear device, in many cases, is a metal piece having conductivity, when the foreign substance MTP is held between the first detection piece 111 and the second detection piece 112, the first line 141 and the third line 143 may be electrically connected to each other by the foreign substance MTP. As a result, electric power may be supplied from the power source 130 to the output portion 120. By using electric power supplied from the power source 130, the output portion 120 may generate a signal indicating that the foreign substance MTP has been held between the first detection piece 111 and the second detection piece 112. Then, the signal may be outputted from the output portion 120 to an external device. Alternatively, it may also be possible that, by using electric power supplied from the power source 130, the output portion 120 issues a warning sound or warning light (namely, information indicating that the detection portion 110A has captured the foreign substance MTP). In this case, the output portion 120 may not need to be connected to the external device. For example, it may also be possible that the output portion 120 is formed of a commonly used speaker device or a commonly used light emitting device (for example, an LED: light emitting diode).

Third Embodiment

The sensors described in relation to the above-mentioned embodiments can be mounted in various types of gear devices. A third embodiment describes an illustrative gear device in which a sensor is mounted.

Figure 3A:
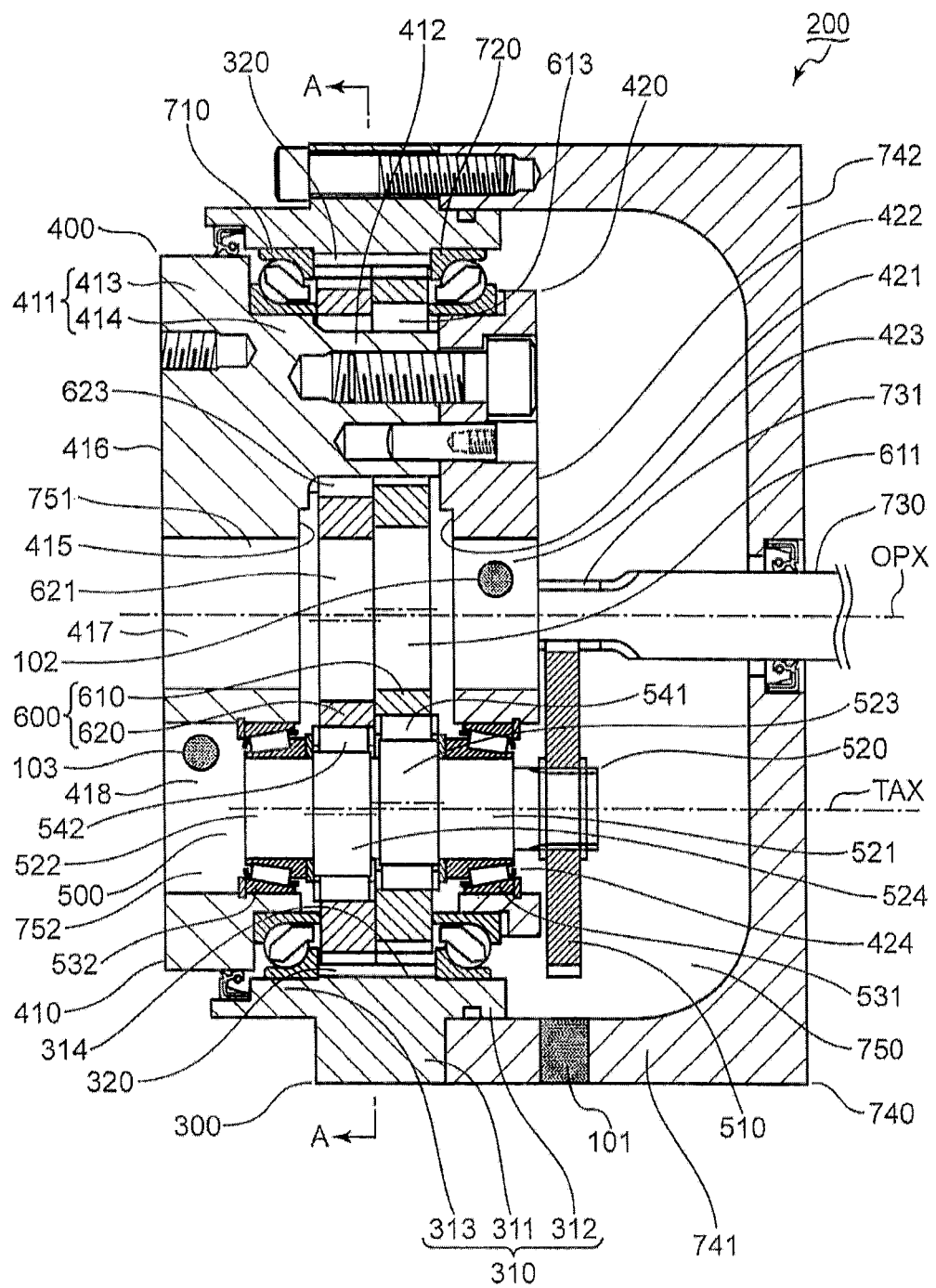
FIG. 3A is a schematic sectional view of a gear device of a third embodiment to a fifth embodiment.
Figure 3B:
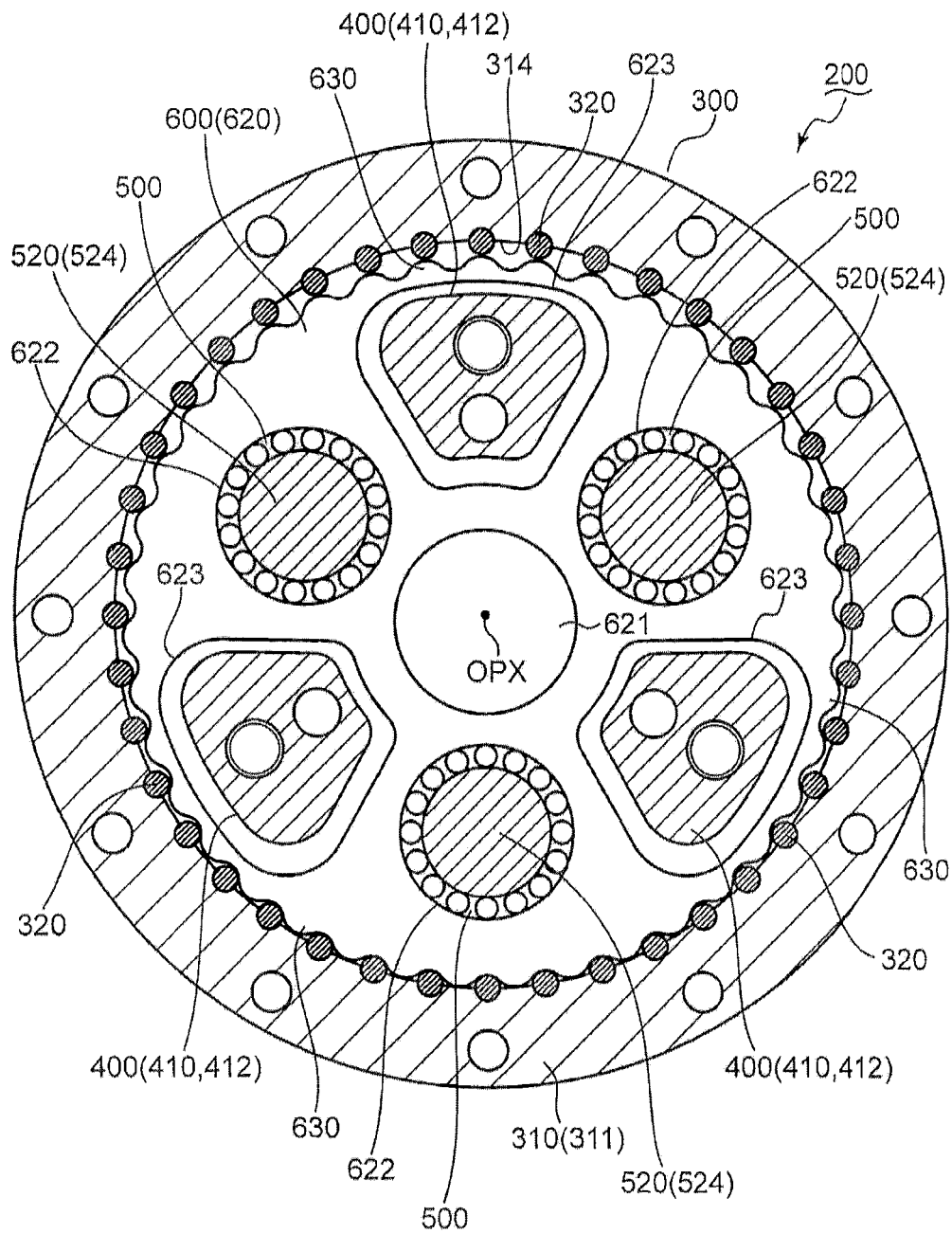
FIG. 3B is a schematic sectional view along a line A-A shown in FIG. 3A.

FIG. 3A is a schematic sectional view of a gear device 200 of the third embodiment. FIG. 3B is a schematic sectional view along a line A-A shown in FIG. 3A. With reference to FIG. 2A to FIG. 3B, a description is given of the gear device 200.

The gear device 200 may be provided with a sensor 101, an outer cylinder 300, a carrier 400, three crank shaft assemblies 500 (FIG. 3A shows one of the three crank shaft assemblies 500), a gear section 600, two main bearings 710 and 720, an input gear 730, and an outer wall 740. It may also be possible that the sensor 101 is formed in conformity with the design principle described in relation to the second embodiment. It may, therefore, also be possible that the description of the second embodiment is applied to the sensor 101.

FIG. 3A shows an output axis OPX. The output axis OPX may correspond to a center axis of each of the two main bearings 710 and 720 and the input gear 730. The outer cylinder 300 and the carrier 400 can relatively rotate about the output axis OPX.

A drive power generated by a motor (not shown) or any other drive source (not shown) may be inputted to each of the three crank shaft assemblies 500 through the input gear 730 extending along the output axis OPX. The drive power inputted to each of the three crank shaft assemblies 500 may be transmitted to the gear section 600 disposed in an internal space surrounded by the outer cylinder 300 and the carrier 400.

As shown in FIG. 3A, the two main bearings 710 and 720 may be fitted into a ring-shaped space formed between the outer cylinder 300 and the carrier 400 surrounded by the outer cylinder 300. By the drive force transmitted to the gear section 600, the outer cylinder 300 and the carrier 400 may be rotated about the output axis OPX.

As shown in FIG. 3A, the outer cylinder 300 may include a substantially cylindrical case 310 and a plurality of internal tooth pins 320. The case 310 may include a first cylindrical portion 311, a second cylindrical portion 312, and a third cylindrical portion 313. The output axis OPX may be a common center axis of the first cylindrical portion 311, the second cylindrical portion 312, and the third cylindrical portion 313. The first cylindrical portion 311 may have an outer diameter larger than those of the second cylindrical portion 312 and the third cylindrical portion 313. The first cylindrical portion 311 may surround the gear section 600. As shown in FIG. 3B, the first cylindrical portion 311 may include an inner circumferential surface 314 on which a plurality of groove portions are formed. The plurality of groove portions may be formed at substantially regular intervals so as to surround the output axis OPX. Each of the plurality of groove portions may be substantially parallel to the output axis OPX. The plurality of internal tooth pins 320 may be fitted into the plurality of groove portions, respectively. Thus, each of the internal tooth pins 320 may be appropriately held by the first cylindrical portion 311.

The second cylindrical portion 312 may be used for joining to the outer wall 740. An appropriate seal member such as an O-ring or any other seal member may be used for sealing between the second cylindrical portion 312 and the outer wall 740. A ring-shaped interstice may be formed between the second cylindrical portion 312 and the carrier 400. The main bearing 720 may be fitted into the ring-shaped interstice. Another ring-shaped interstice may be formed between the third cylindrical portion 313 and the carrier 400. The main bearing 710 may be fitted into the interstice between the third cylindrical portion 313 and the carrier 400. As a result, the carrier 400 may become relatively rotatable with respect to the outer cylinder 300.

As shown in FIG. 3B, the plurality of internal tooth pins 320 may be disposed around the output axis OPX at substantially regular intervals. Each of the plurality of internal tooth pins 320 may have a half circumferential surface projecting from an inner wall of the case 310 toward the output axis OPX. Thus, the plurality of internal tooth pins 320 may serve as a plurality of internal teeth meshed with the gear section 600. In this embodiment, the plurality of internal tooth pins 320 may be an example of the plurality of internal teeth.

As shown in FIG. 3A, the carrier 400 may include a base portion 410 and an end plate 420. The carrier 400 as a whole may have a cylindrical shape. The end plate 420 may be substantially disc-shaped. A circumferential surface of the end plate 420 may be partially surrounded by the second cylindrical portion 312. The main bearing 720 may be fitted into a ring-shaped interstice between the second cylindrical portion 312 and the circumferential surface of the end plate 420.

The base portion 410 may include a base plate portion 411 (see FIG. 3A) and three shaft portions 412 (see FIG. 3B). The base plate portion 411 may include a first disc portion 413 and a second disc portion 414. The second disc portion 414 may be positioned between the first disc portion 413 and the end plate 420. The second disc portion 414 may be smaller in diameter than the first disc portion 413. Each of the three shaft portions 412 may extend from the second disc portion 414 toward the end plate 420.

A circumferential surface of the second disc portion 414 may be surrounded by the third cylindrical portion 313. The main bearing 710 may be fitted into a ring-shaped interstice between the third cylindrical portion 313 and the circumferential surface of the second disc portion 414. The third cylindrical portion 313 may partially surround a circumferential surface of the first disc portion 413. An appropriate seal member such as a seal ring or any other seal member may be fitted into a ring-shaped interstice between the third cylindrical portion 313 and the circumferential surface of the first disc portion 413.

In an extending direction of the output axis OPX, the base place portion 411 may be provided away from the end plate 420. The base plate portion 411 may be substantially coaxial with the end plate 420. That is, the output axis OPX may correspond to a center axis of each of the base plate portion 411 and the end plate 420.

The second disc portion 414 may include an inner surface 415 opposed to the gear section 600. The first disc portion 413 may include an outer surface 416 on an opposite side to the inner surface 415. The inner surface 415 and the outer surface 416 may extend along a virtual plane (not shown) orthogonal to the output axis OPX.

A central through hole 417 (see FIG. 3A) and three holding through holes 418 (FIG. 3A shows one of the three holding through holes 418) may be formed through the base plate portion 411. The central through hole 417 may extend between the inner surface 415 and the outer surface 416 along the output axis OPX. The output axis OPX may correspond to a center axis of the central through hole 417. On a virtual circle (not shown) about the output axis OPX, respective centers of the three holding through holes 418 may be disposed at substantially equal intervals.

FIG. 3A shows a transmission axis TAX in addition to the output axis OPX. The transmission axis TAX may be defined at a position away from the output axis OPX. The transmission axis TAX may be substantially parallel to the output axis OPX. Each of the holding though holes 418 may extend between the inner surface 415 and the outer surface 416 along the transmission axis TAX. The transmission axis TAX may correspond to a rotation center axis of each of the crank shaft assemblies 500 and a center axis of each of the holding through holes 418. The crank shaft assemblies 500 may be partially disposed in the holding through holes 418, respectively.

The end plate 420 may include an inner surface 421 and an outer surface 422 on an opposite side to the inner surface 421. The inner surface 421 may be opposed to the gear section 600. The inner surface 421 and the outer surface 422 may extend along a virtual plane (not shown) orthogonal to the output axis OPX.

A central through hole 423 (see FIG. 3A) and three holding through holes 424 (FIG. 3A shows one of the three holding through holes 424) may be formed through the end plate 420. The central through hole 423 may extend between the inner surface 421 and the outer surface 422 along the output axis OPX. The output axis OPX may correspond to a center axis of the central through hole 423. On a virtual circle (not shown) about the output axis OPX, respective centers of the three holding through holes 424 may be disposed at substantially equal intervals. Each of the three holding though holes 424 may extend between the inner surface 421 and the outer surface 422 along the transmission axis TAX. The transmission axis TAX may correspond to a center axis of each of the holding through holes 424. The crank shaft assemblies 500 may be partially disposed in the holding through holes 424, respectively. The three holding through holes 424 formed through the end plate 420 may be coaxial with the three holding through holes 418 formed through the base plate portion 411, respectively.

Each of the three shaft portions 412 may extend from the inner surface 415 of the second disc portion 414 toward the inner surface 421 of the end plate 420. The end plate 420 may be connected to a tip end surface of each of the three shaft portions 412. It may also be possible that the end plate 420 is connected to the tip end surface of each of the three shaft portions 412 with a reamer bolt or a positioning pin or by any other appropriate fixing technique. A principle of this embodiment may not be limited to a particular connection technique used for connection between the end plate 420 and each of the three shaft portions 412.

As shown in FIG. 3A, the gear section 600 may be disposed between the inner surface 415 of the second disc portion 414 and the inner surface 421 of the end plate 420. The three shaft portions 412 may extend through the gear section 600 to be connected to the end plate 420.

As shown in FIG. 3A, the gear section 600 may include two oscillating gears 610 and 620. The oscillating gear 610 may be disposed between the end plate 420 and the oscillating gear 620. The oscillating gear 620 may be disposed between the base plate portion 411 and the oscillating gear 610. It may also be possible that the oscillating gears 610 and 620 are formed based on a common design drawing. It may also be possible that each of the oscillating gears 610 and 620 is a trochoidal gear or a cycloidal gear. The principle of this embodiment may not be limited to a particular type of gear used as each of the oscillating gears 610 and 620.

Each of the oscillating gears 610 and 620 may include a plurality of external teeth 630 (see FIG. 3B) projecting toward the inner wall of the case 310. When each of the crank shaft assemblies 500 rotates about the transmission axis TAX, the oscillating gears 610 and 620 may perform orbital movement (namely, oscillating rotation) within the case 310 with the plurality of external teeth 630 being meshed with the plurality of internal tooth pins 320. During this time, respective centers of the oscillating gears 610 and 620 may orbit about the output axis OPX. Relative rotation between the outer cylinder 300 and the carrier 400 may be caused by oscillating rotation of the oscillating gears 610 and 620.

A central through hole 611 may be formed at the center of the oscillating gear 610. A central through hole 621 may be formed at the center of the oscillating gear 620. The central through hole 611 may communicate with the central through hole 423 of the end plate 420 and the central through hole 621 of the oscillating gear 620. The central through hole 621 may communicate with the central through hole 417 of the base plate portion 411 and the central through hole 611 of the oscillating gear 610.

As shown in FIG. 3B, three circular through holes 622 may be formed through the oscillating gear 620. Similarly, three circular through holes may be formed through the oscillating gear 610. In cooperation with the holding through holes 418 of the base plate portion 411 and the holding through holes 424 of the end plate 420, the circular through holes 622 of the oscillating gear 620 and the circular through holes of the oscillating gear 610 may form housing spaces in which the crank shaft assemblies 500 are housed, respectively.

Three trapezoidal through holes 613 (FIG. 3A shows one of the three trapezoidal through holes 613) may be formed through the oscillating gear 610. Three trapezoidal through holes 623 (see FIG. 3B) may be formed through the oscillating gear 620. The shaft portions 412 of the carrier 400 may extend through the trapezoidal through holes 613 and 623. The trapezoidal through holes 613 and 623 may have a size set so as not to interfere with the shaft portions 412.

Each of the three crank shaft assemblies 500 may include a transmission gear 510, a crank shaft 520, two journal bearings 531 and 532, and two crank bearings 541 and 542. The transmission gear 510 may be meshed with the input gear 730. In accordance with rotation of the input gear 730, the transmission gear 510 may rotate about the transmission axis TAX.

The crank shaft 520 may include a first journal 521, a second journal 522, a first eccentric portion 523, and a second eccentric portion 524. The first journal 521 may extend along the transmission axis TAX and be inserted into each of the holding through holes 424 of the end plate 420. On an opposite side to the first journal 521, the second journal 522 may extend along the transmission axis TAX and be inserted into each of the holding through holes 418 of the base plate portion 411. The journal bearing 531 may be fitted into a ring-shaped space between the first journal 521 and an inner wall of the end plate 420, which forms each of the holding through holes 424. As a result, the first journal 521 may be joined to the end plate 420. The journal bearing 532 may be fitted into a ring-shaped space between the second journal 522 and an inner wall of the base plate portion 411, which forms each of the holding through holes 418. As a result, the second journal 522 may be joined to the base plate portion 411. Accordingly, the carrier 400 can support the crank shaft assemblies 500.

The first eccentric portion 523 may be positioned between the first journal 521 and the second eccentric portion 524. The second eccentric portion 524 may be positioned between the second journal 522 and the first eccentric portion 523. The crank bearing 541 may be fitted into a ring-shaped space between the first eccentric portion 523 and an inner wall of the oscillating gear 610, which forms each of the circular through holes. As a result, the oscillating gear 610 may be mounted to the first eccentric portion 523. The crank bearing 542 may be fitted into a ring-shaped space between the second eccentric portion 524 and an inner wall of the oscillating gear 620, which forms each of the circular through holes 622. As a result, the oscillating gear 620 may be mounted to the second eccentric portion 524.

The first journal 521 may be coaxial with the second journal 522 and rotate about the transmission axis TAX. Each of the first eccentric portion 523 and the second eccentric portion 524 may be formed in a cylindrical column shape and positioned eccentrically from the transmission axis TAX. The first eccentric portion 523 and the second eccentric portion 524 may eccentrically rotate with respect to the transmission axis TAX and impart oscillating rotation to the oscillating gears 610 and 620, respectively. In this embodiment, one of the first eccentric portion 523 and the second eccentric portion 524 may be an example of an eccentric portion.

When the outer cylinder 300 is fixed, since the oscillating gears 610 and 620 may be meshed with the plurality of internal tooth pins 320 of the outer cylinder 300, oscillating rotation of the oscillating gears 610 and 620 may be converted into orbital motion of the crank shaft 520 about the output axis OPX. The end plate 420 and the base plate portion 411 may be joined to the first journal 521 and the second journal 522, respectively, and thus the orbital motion of the crank shaft 520 may be converted into rotary motion of each of the end plate 420 and the base plate portion 411 about the output axis OPX. An orbital phase difference between the oscillating gears 610 and 620 may be determined by a difference in eccentricity direction between the first eccentric portion 523 and the second eccentric portion 524.

When the carrier 400 is fixed, since the oscillating gears 610 and 620 may be meshed with the plurality of internal tooth pins 320 of the outer cylinder 300, oscillating rotation of the oscillating gears 610 and 620 may be converted into rotary motion of the outer cylinder 300 about the output axis OPX.

The input gear 730 may extend along the output axis OPX. A gear portion 731 may be formed at a tip end portion of the input gear 730. The gear portion 731 may be meshed with the transmission gear 510. When the gear portion 731 rotates about the output axis OPX, the transmission gear 510 may rotate about the transmission axis TAX. As a result, the crank shaft 520 to which the transmission gear 510 is fixed may rotate to cause oscillating rotation of the oscillating gears 610 and 620.

The outer wall 740 may include a joint wall 741 and a support wall 742. The joint wall 741 may be a cylindrical body surrounding the input gear 730. The joint wall 741 may be fitted over the second cylindrical portion 312. As a result, the joint wall 741 may be joined to the outer cylinder 300.

In cooperation with the joint wall 741 and the end plate 420, the support wall 742 may form a detection space 750. That is, a boundary of the detection space 750 may be formed mainly by respective wall surfaces of the joint wall 741, the end plate 420, and the support wall 742.

While the joint wall 741 may extend along the output axis OPX, the support wall 742 may extend substantially orthogonally to the output axis OPX and be opposed to the outer surface 422 of the end plate 420. The support wall 742 may close a circular opening portion formed by the joint wall 741. On an opposite side to the support wall 742, the end plate 420 may partially close the circular opening portion formed by the joint wall 741. In this embodiment, the end plate 420 may be an example of a first end wall.

A though hole may be formed through the joint wall 741 along the output axis OPX. An oil seal may be fitted into the through hole. The input gear 730 may be inserted into the oil seal, and the gear portion 731 may be disposed in the detection space 750. As a result, the support wall 742 can appropriately support the input gear 730.

The input gear 730 may rotate at an rpm higher than those of the other gears (namely, the transmission gear 510 and the oscillating gears 610 and 620). Accordingly, a metal piece peeled off from respective tooth surfaces of the input gear 730 and the transmission gear 510 may be likely to float in a lubricant encapsulated in the detection space 750.

The sensor 101 may be mounted to the joint wall 741. Alternatively, it may also be possible that the sensor is mounted to the support wall 742.

The detection portion 110A described with reference to FIG. 2A and FIG. 2B may be disposed in the detection space 750. On the other hand, it may also be possible that the output portion 120 and the power source 130 are disposed at other parts, For example, it may also be possible that the output portion 120 and the power source 130 are fitted into a through hole formed through the outer wall 740. Alternatively, it may also be possible that the output portion 120 and the power source 130 are mounted to an outer surface of the outer wall 740. Yet alternatively, it may also be possible that the output portion 120 and the power source 130 are disposed at positions away from the outer cylinder 300, the carrier 400, and the outer wall 740.

High-speed rotation of each of the input gear 730 and the transmission gear 510 may cause a vigorous flow of the lubricant in the detection space 750. Accordingly, the detection portion 110A of the sensor 101 may easily capture a large foreign substance (for example, a metal piece peeled off from the respective tooth surfaces of the input gear 730 and the transmission gear 510) floating in the lubricant in the detection space 750.

In this embodiment, it may also be possible that while the outer cylinder 300 is fixed, the carrier 400 is rotated When the outer cylinder 300 is fixed, the outer wall 740 may also be fixed. As a result, electrical wiring between an external device and the sensor 101 may be simplified.

When the outer cylinder 300 is fixed, it may also be possible that the sensor 101 is disposed below a meshed portion between the gear portion 731 and the transmission gear 510. A large foreign substance generated from the gear portion 731 and the transmission gear 510 may move downward by gravity and thus be more easily captured by the detection portion 110A.

Fourth Embodiment

The gear device described in relation to the third embodiment may be provided with the sensor that detects a foreign substance in the detection space surrounded by the carrier and the outer wall. Additionally or alternatively, it may also be possible that the gear device is provided with a sensor that detects a foreign substance in another detection space. In a space on a periphery of the output axis, the sensor may lie next to not only the input gear but also the various components such as the oscillating gears and the crank shaft assemblies. Accordingly, in a case where the sensor detects a foreign substance in such a space on the periphery of the output axis, an increase in malfunction risk in various parts of the gear device can be detected. A fourth embodiment describes an illustrative gear device in which a sensor that detects a foreign substance on a periphery of an output axis is mounted.

As shown in FIG. 3A, the gear device 200 may be provided with a sensor 102. It may also be possible that the sensor 102 is formed in conformity with the design principle described in relation to the second embodiment. It may, therefore, also be possible that the description of the second embodiment is applied to the sensor 102.

As described in relation to the third embodiment, the central through holes 417 and 423 of the carrier 400 and the central through holes 611 and 621 of the gear section 600 may be continuous with each other along the output axis OPX to from one detection space 751. That is, a boundary of the detection space 751 may be formed mainly by the carrier 400 and the gear section 600.

The outer surface 416 of the carrier 400 may be pressed against a counterpart member (not shown). Accordingly, the detection space 751 may be closed by the counterpart member. As a result, a lubricant in the detection space 751 may be enclosed in the gear device 200.

The detection portion 110A (see FIG. 2A and FIG. 2B) of the sensor 102 may be disposed in the detection space 751. When, while the outer cylinder 300 is fixed, the carrier 400 is rotated, it may also be possible that the detection portion 110A is held away from the carrier 400 by a highly rigid conductive member. In this case, it may also be possible that the conductive member extends toward the outer wall 740 and is electrically connected to the output portion 120 (see FIG. 2A and FIG. 2B) and the power source 130 (see FIG. 2A and FIG. 2B), which are disposed outside the detection space 750.

When, while the carrier 400 is fixed, the outer cylinder 300 is rotated, it may also be possible that the detection portion 110A is mounted to the base plate portion 411 or the end plate 420. In this case, it may also be possible that the conductive member is electrically connected from the detection portion 110A to the output portion 120 and the power source 130, which are mounted to the counterpart member.

Fifth Embodiment

Among the components of the gear devices described in relation to the third embodiment and the fourth embodiment, the crank shaft assemblies may have the most complicated structure. Accordingly, the crank shaft assemblies may be exposed to a high breakage risk. In a case where the sensor is disposed near the crank shaft assemblies, an increase in breakage risk of the crank shaft assemblies may be easily and instantaneously detected. A fourth embodiment describes an illustrative gear device having a sensor disposed near crank shaft assemblies.

As shown in FIG. 3A, the gear device 200 may be provided with a sensor 103. It may also be possible that the sensor 103 is formed in conformity with the design principle described in relation to the second embodiment. It may, therefore, also be possible that the description of the second embodiment is applied to the sensor 103.

As described in relation to the third embodiment, the three holding through hole 418 (FIG. 3A shows one of the three holding through holes 418) may be formed through the base plate portion 411. The second journal 522 may extend from the second eccentric portion 524 along the transmission axis TAX and be inserted into a corresponding one of the holding through holes 418. As a result, the second journal 522 may make up a part of each of the holding through holes 418. In this embodiment, the base plate portion 411 may be an example of a second end plate. Each of the holding through holes 418 may be an example of a through hole.

The detection portion 110A (see FIG. 2A and FIG. 2B) of the sensor 103 may be disposed in a remaining region of one of the holding through holes 418 (a region not occupied by the second journal 522). The region of one of the holding through holes 418 not occupied by the second journal 522 may be used as a detection space 752. An outline of the detection space 752 may be formed mainly by the base plate portion 411.

As described in relation to the fourth embodiment, the outer surface 416 of the carrier 400 may be pressed against a counterpart member (not shown), and thus a lubricant in the detection space 752 may be enclosed in the gear device 200.

With regard to this embodiment, it may be preferable that, while the carrier 400 is fixed, the outer cylinder 300 is rotated. The detection portion 110A may be mounted to the base plate portion 411. A conductive member may be electrically connected from the detection portion 110A to the output portion 120 and the power source 130, which are mounted to the counterpart member.

Sixth Embodiment

The sensor described in relation to the fifth embodiment may be disposed near an end portion of one of the crank shaft assemblies. Alternatively, it may also be possible that the sensor is disposed near a center of one of the crank shaft assemblies in an axial length direction of the crank shaft assemblies. In this case, an increase in breakage risk of the crank shaft assemblies can be detected with high accuracy. A sixth embodiment describes an illustrative gear device in which a sensor is mounted near a center of one of crank shaft assemblies.

Figure 4A:
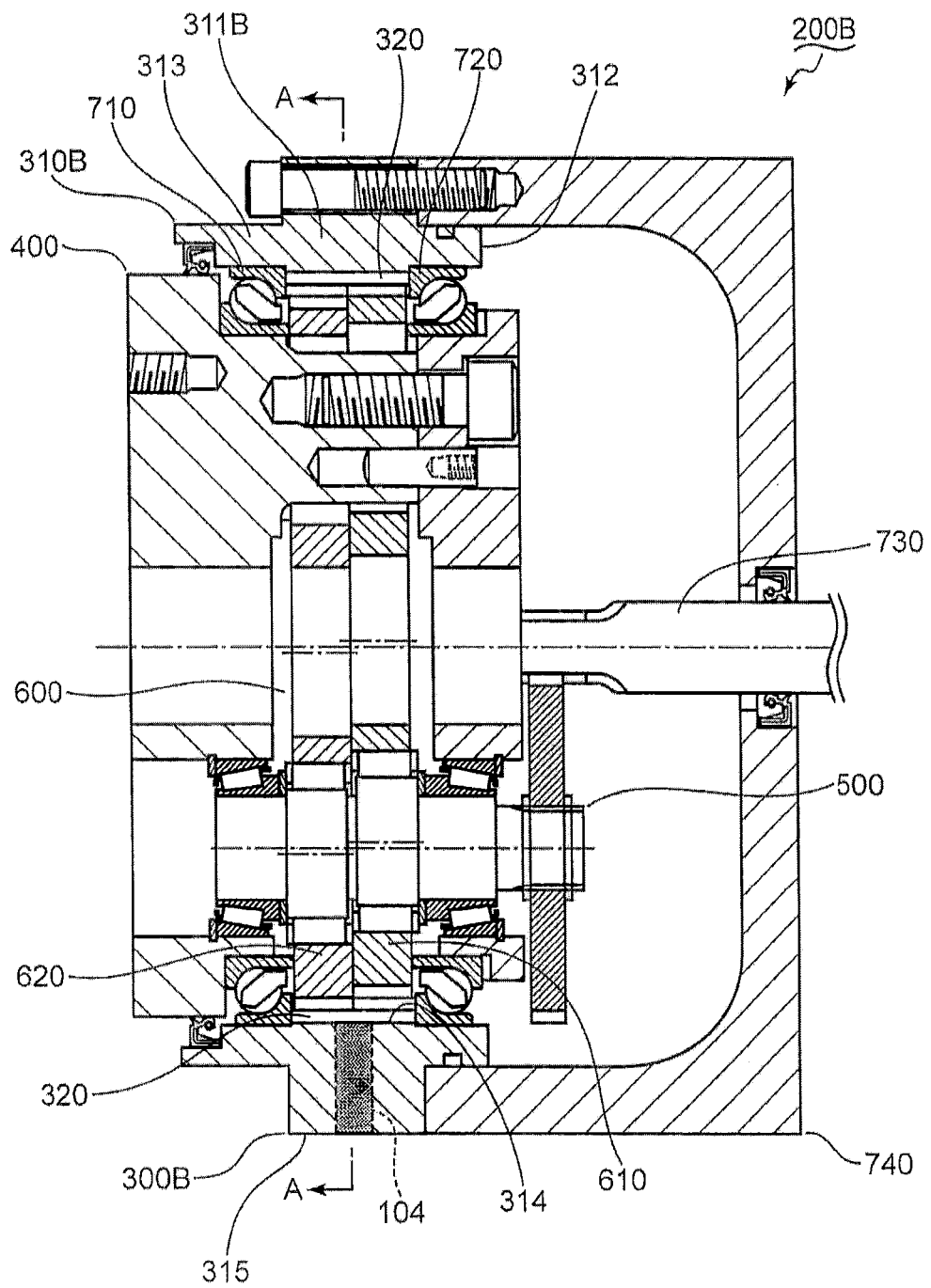
FIG. 4A is a schematic sectional view of a gear device of a sixth embodiment.
Figure 4B:
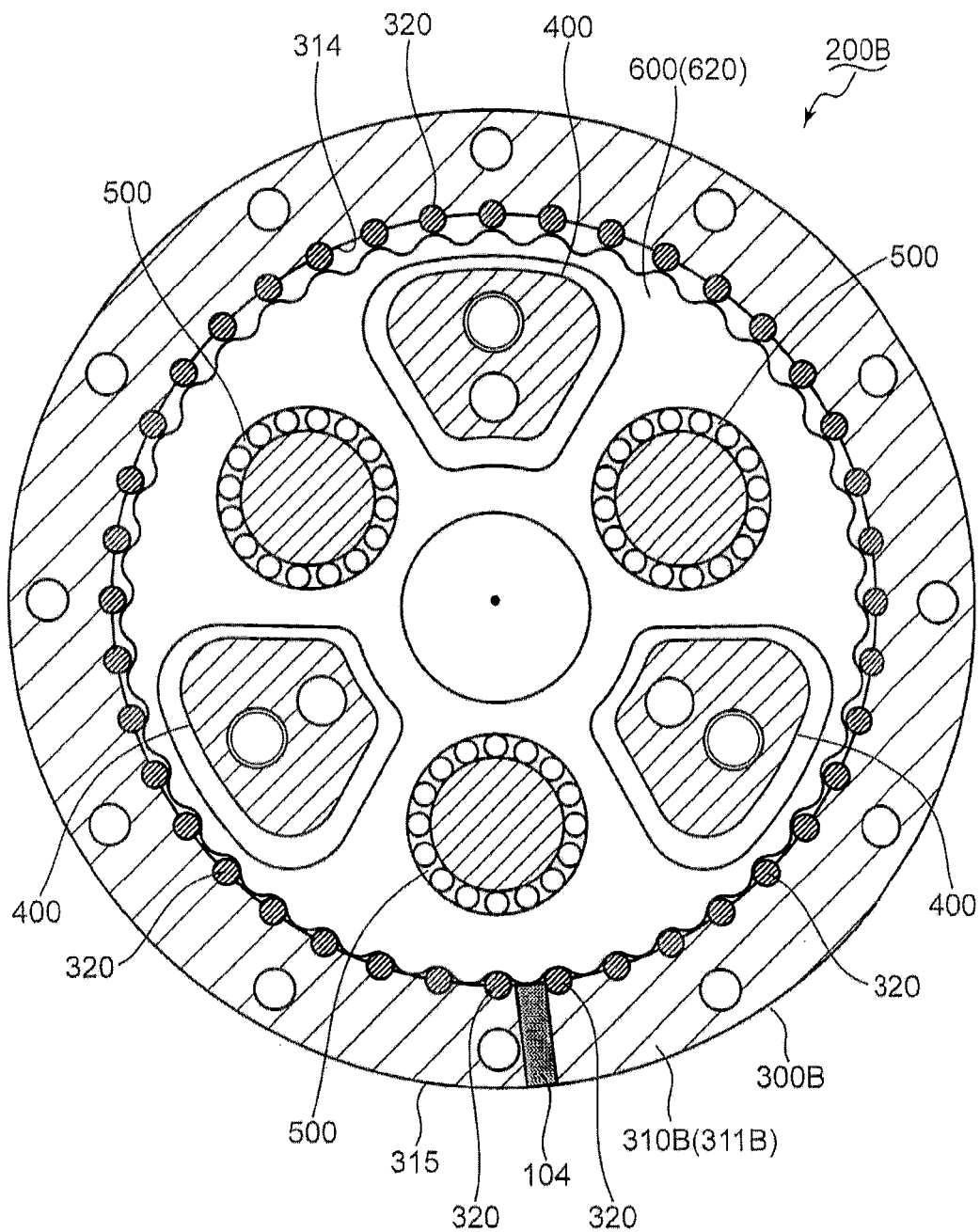
FIG. 4B is a schematic sectional view along a line A-A shown in FIG. 4A.

FIG. 4A is a schematic sectional view of a gear device 200B of the sixth embodiment. FIG. 4B is a schematic sectional view along a line A-A shown in FIG. 4A. With reference to FIG. 2A, FIG. 2B, FIG. 4A, and FIG. 4B, a description is given of the gear device 200B. The description of the third embodiment may be applied to elements denoted by the same reference characters as those in the third embodiment.

Similarly to the third embodiment, the gear device 200B may be provided with a carrier 400, three crank shaft assemblies 500 (FIG. 4A shows one of the three crank shaft assemblies 500), a gear section 600, two main bearings 710 and 720, an input gear 730, and an outer wall 740. The description of the third embodiment may be applied to these elements.

The gear device 200B may be provided further with a sensor 104 and an outer cylinder 300B. It may also be possible that the sensor 104 is formed in conformity with the design principle described in relation to the second embodiment. It may, therefore, also be possible that the description of the second embodiment is applied to the sensor 104.

Similarly to the third embodiment, the outer cylinder 300B may include a plurality of internal tooth pins 320. The description of the third embodiment may be applied to the plurality of internal tooth pins 320.

The outer cylinder 300B may further include a substantially cylindrical case 310B. Similarly to the third embodiment, the case 310B may include a second cylindrical portion 312 and a third cylindrical portion 313. The description of the third embodiment may be applied to these elements.

The case 310B may further include a first cylindrical portion 311B. Similarly to the third embodiment, the first cylindrical portion 311B may include an inner circumferential surface 314. The description of the third embodiment may be applied to the inner circumferential surface 314.

The first cylindrical portion 311B may include an outer circumferential surface 315 surrounding the inner circumferential surface 314. A through hole extending between the inner circumferential surface 314 and the outer circumferential surface 315 may be formed through the first cylindrical portion 311B. By using this through hole, the sensor 104 may be mounted in the first cylindrical portion 311B.

The detection portion 110A (see FIG. 2A and FIG. 2B) of the sensor 104 may be embedded in the through hole in a vicinity of the inner circumferential surface 314. As a result, the detection portion 110A can hold, in a sandwiching manner, a large foreign substance that has fallen into the through hole. In a vicinity of the outer circumferential surface 315, the through hole may be closed with an appropriate encapsulating agent non-reactive with a lubricant, such as a resin or any other encapsulating agent. As a result, the lubricant may be enclosed in the gear device 200B. In this embodiment, a lubricant filling region on a periphery of the detection portion 110A may be an example of the detection space. An outline of the detection space may be formed mainly by respective circumferential surfaces of the inner circumferential surface 314 and oscillating gears 610 and 620.

It may also be possible that the output portion 120 (see FIG. 2A and FIG. 2B) and the power source 130 (see FIG. 2A and FIG. 2B) are embedded in the through hole near the outer circumferential surface 315. Alternatively, it may also be possible that the output portion 120 and the power source 130 are mounted to an outer surface of the outer cylinder 300B.

With regard to this embodiment, it may be preferable that, while the outer cylinder 300B is fixed, the carrier 400 is rotated. In this case, it may also be possible that the outer cylinder 300B is fixed so that the detection portion 110A is positioned below an output axis OPX. A large foreign substance may move downward by gravity and eventually be held in a sandwiched manner by the detection portion 110A.

Seventh Embodiment

The gear devices described in relation to the above-mentioned embodiments may have the crank shaft assemblies provided to extend along the transmission axis away from the output axis. Alternatively, it may also be possible that the gear device has a crank shaft assembly provided to extend along the output axis. Such a crank shaft assembly can be mounted in various types of gear devices. A seventh embodiment describes an illustrative gear device having a crank shaft assembly provided to extend along an output axis.

Figure 5:
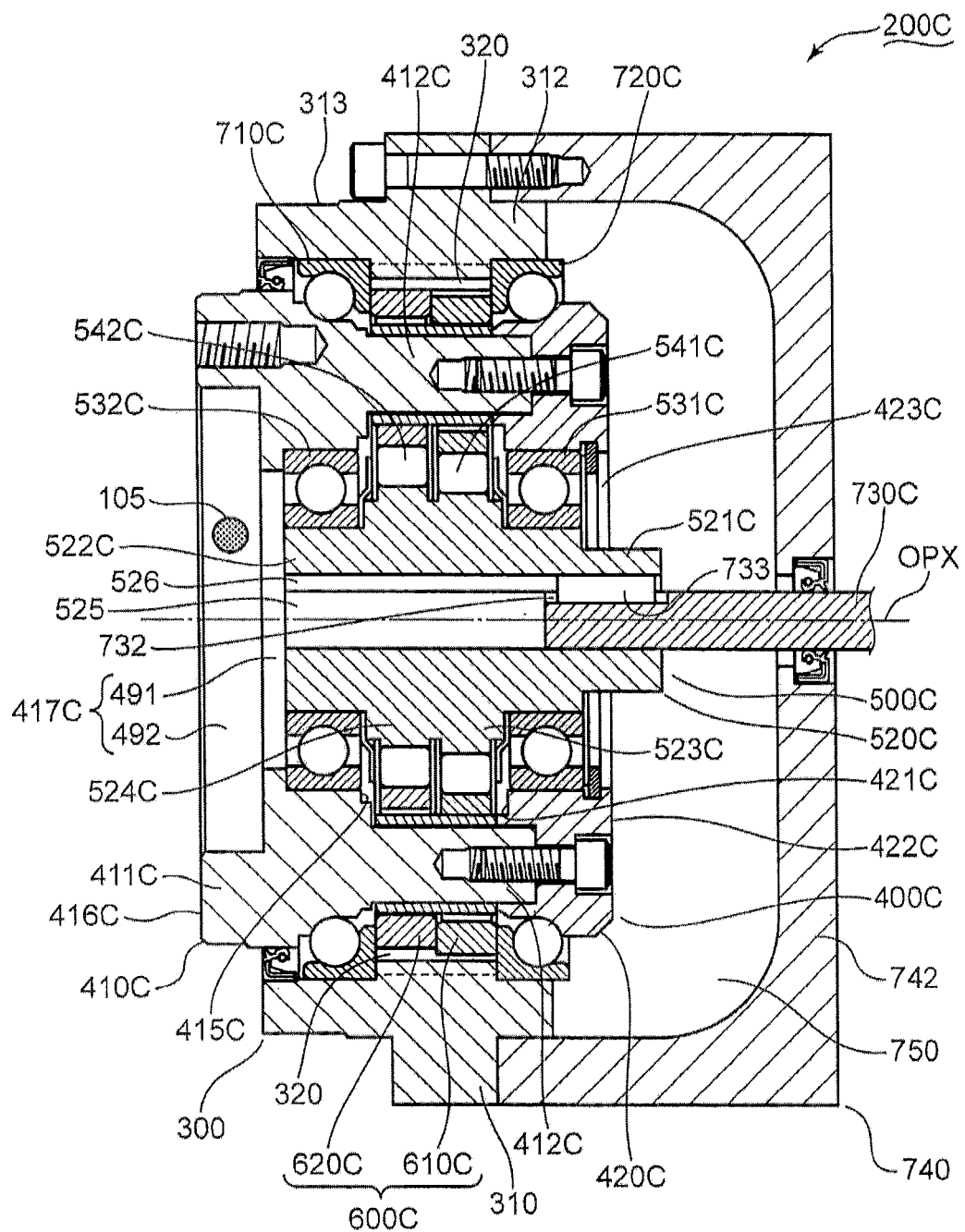
FIG. 5 is a schematic sectional view of a gear device of a seventh embodiment.

FIG. 5 is a schematic sectional view of a gear device 200C of the seventh embodiment. With reference to FIG. 2A, FIG. 2B, and FIG. 5, a description is given of the gear device 200C. The description of the third embodiment may be applied to elements denoted by the same reference characters as those in the third embodiment.

Similarly to the third embodiment, the gear device 200C may be provided with an outer cylinder 300 and an outer wall 740. The description of the third embodiment may be applied to these elements.

The gear device 200C may be provided with a sensor 105, a carrier 400C, a crank shaft assembly 500C, a gear section 600C, two main bearings 710C and 720C, and an input gear 730C. It may also be possible that the sensor 105 is formed in conformity with the design principle described in relation to the second embodiment. It may, therefore, also be possible that the description of the second embodiment is applied to the sensor 105.

FIG. 5 shows an output axis OPX. The output axis OPX may correspond to a center axis of each of the two main bearings 710C and 720C and the input gear 730C. The outer cylinder 300 and the carrier 400C can relatively rotate about the output axis OPX.

A drive power generated by a motor (not shown) or any other drive source (not shown) may be inputted to the crank shaft assembly 500C through the input gear 730C extending along the output axis OPX. The drive power inputted to the crank shaft assembly 500C may be transmitted to the gear section 600C disposed in an internal space surrounded by the outer cylinder 300 and the carrier 400C.

As shown in FIG. 5, the two main bearings 710C and 720C may be fitted into a ring-shaped space formed between the outer cylinder 300 and the carrier 400C surrounded by the outer cylinder 300. By the drive force transmitted to the gear section 600C, the outer cylinder 300 or the carrier 400C may be rotated about the output axis OPX.

As shown in FIG. 5, the carrier 400 may include a base portion 410C and an end plate 420C. The carrier 400C as a whole may have a cylindrical shape. The end plate 420C may be substantially disc-shaped. An outer circumferential surface of the end plate 420C may be partially surrounded by a second cylindrical portion 312. The main bearing 720C may be fitted into a ring-shaped interstice between the second cylindrical portion 312 and a circumferential surface of the end plate 420C. An outer circumferential surface of the end plate 420C may be formed so that a roller of the main bearing 720C rolls directly on the end plate 420C.

The base portion 410C may include a base plate portion 411C and a plurality of shaft portions 412C. An outer circumferential surface of the base plate portion 411C may be partially surrounded by a third cylindrical portion 313. The main bearing 710C may be fitted into a ring-shaped interstice between the third cylindrical portion 313 and the outer circumferential surface of the base plate portion 411C. The outer circumferential surface of the base plate portion 411C may be formed so that a roller of the main bearing 710C rolls directly on the outer circumferential surface of base plate portion 411C.

In an extending direction of the output axis OPX, the base place portion 411C may be provided away from the end plate 420C. The base plate portion 411C may be substantially coaxial with the end plate 420C. That is, the output axis OPX may correspond to a center axis of each of the base plate portion 411C and the end plate 420C.

The base plate portion 411C may include an inner surface 415C and an outer surface 416C on an opposite side to the inner surface 415C. The inner surface 415C may be opposed to the gear section 600C. The inner surface 415C and the outer surface 416C may extend along a virtual plane (not shown) orthogonal to the output axis OPX.

A central through hole 417C may be formed through the base plate portion 411C. The central through hole 417C may extend between the inner surface 415C and the outer surface 416C along the output axis OPX. The output axis OPX may correspond to a center axis of the central through hole 417C.

The end plate 420C may include an inner surface 421C and an outer surface 422C on an opposite side to the inner surface 421C. The inner surface 421C may be opposed to the gear section 600C. The inner surface 421C and the outer surface 422C may extend along a virtual plane (not shown) orthogonal to the output axis OPX.

A central through hole 423C may be formed through the end plate 420C. The central through hole 423C may extend between the inner surface 421C and the outer surface 422C along the output axis OPX. The output axis OPX may correspond to a center axis of the central through hole 423C.

Each of the plurality of shaft portions 412C may extend from the inner surface 415C of the base plate portion 411C toward the inner surface 421C of the end plate 420C. The end plate 420C may be connected to a tip end surface of each of the plurality of shaft portions 412C. It may also be possible that the end plate 420C is connected to the tip end surface of each of the plurality of shaft portions 412C with a reamer bolt or a positioning pin or by any other appropriate fixing technique. A principle of this embodiment may not be limited to a particular connection technique used for connection between the end plate 420C and each of the plurality of shaft portions 412C.

As shown in FIG. 5, the gear section 600 may be disposed between the inner surface 415C of the base plate portion 411C and the inner surface 421C of the end plate 420C. The plurality of shaft portions 412C may extend through the gear section 600C to be connected to the end plate 420C.

As shown in FIG. 5, the gear section 600C may include two oscillating gears 610C and 620C. The oscillating gear 610C may be disposed between the end plate 420C and the oscillating gear 620C. The oscillating gear 620C may be disposed between the base plate portion 411C and the oscillating gear 610C. It may also be possible that the oscillating gears 610C and 620C are formed based on a common design drawing, It may also be possible that each of the oscillating gears 610C and 620C is a trochoidal gear or a cycloidal gear. The principle of this embodiment may not be limited to a particular type of gear used as each of the oscillating gears 610C and 620C.

Each of the oscillating gears 610C and 620C may be meshed with a plurality of internal tooth pins 320. When the crank shaft assembly 500C rotates about the output axis OPX, the oscillating gears 610C and 620C may perform orbital movement (namely, oscillating rotation) within a case 310 while being meshed with the internal tooth pins 320. During this time, respective centers of the oscillating gears 610C and 620C may orbit about the output axis OPX. Relative rotation between the outer cylinder 300 and the carrier 400C may be caused by oscillating rotation of the oscillating gears 610C and 620C.

A through hole may be formed through each of the oscillating gears 610C and 620C at a center thereof. The crank shaft assembly 500C may be fitted into the through hole formed through each of the oscillating gears 610C and 620C at the center thereof.

A plurality of through holes may be formed through each of the oscillating gears 610C and 620C so as to correspond to the plurality of shaft portions 412C disposed along a virtual circle defined around the output axis OPX. The plurality of shaft portions 412C may be inserted into these through holes, respectively. These through holes may have a size set so that there occurs no interference between the plurality of shaft portions 412C and the oscillating gears 610C and 620C.

The crank shaft assembly 500C may include a crank shaft 520C, two journal bearings 531C and 532C, and two crank bearings 541C and 542C. The crank shaft 520C may include a first journal 521C, a second journal 522C, a first eccentric portion 523C, and a second eccentric portion 524C. The first journal 521C may extend along the output axis OPX and be inserted into the central through hole 423C of the end plate 420C. On an opposite side to the first journal 521C, the second journal 522C may extend along the output axis OPX and be inserted into the central through hole 417C of the base plate portion 411C. The journal bearing 531C may be fitted into a ring-shaped space between the first journal 521C and an inner wall of the end plate 420C, which forms the central through hole 423C. As a result, the first journal 521C may be joined to the end plate 420C. The journal bearing 532C may be fitted into a ring-shaped space between the second journal 522C and an inner wall of the base plate portion 411C, which forms the central through hole 417C. As a result, the second journal 522C may be joined to the base plate portion 411C. Accordingly, the carrier 400C can support the crank shaft assembly 500C. In this embodiment, the end plate 420C may be an example of the first end wall. The base plate portion 411C may be an example of the second end plate.

The first eccentric portion 523C may be positioned between the first journal 521C and the second eccentric portion 524C. The second eccentric portion 524C may be positioned between the second journal 522C and the first eccentric portion 523C. The crank bearing 541C may be fitted into the through hole formed through the oscillating gear 610C at the center thereof and joined to the first eccentric portion 523C. As a result, the oscillating gear 610C may be mounted to the first eccentric portion 523C. The crank bearing 542C may be fitted into the through hole formed through the oscillating gear 620C at the center thereof and joined to the second eccentric portion 524C. As a result, the oscillating gear 620C may be mounted to the second eccentric portion 524C.

The first journal 521C may be substantially coaxial with the second journal 522C and rotate about the output axis OPX. Each of the first eccentric portion 523C and the second eccentric portion 524C may be formed in a cylindrical column shape and positioned eccentrically from the output axis OPX. The first eccentric portion 523C and the second eccentric portion 524C may eccentrically rotate with respect to the output axis OPX and impart oscillating rotation to the oscillating gears 610C and 620C, respectively. In this embodiment, one of the first eccentric portion 523C and the second eccentric portion 524C may be an example of the eccentric portion.

When the outer cylinder 300 is fixed, since the oscillating gears 610C and 620C may be meshed with the plurality of internal tooth pins 320 of the outer cylinder 300, oscillating rotation of the oscillating gears 610C and 620C may be converted into orbital motion of the crank shaft 520C about the output axis OPX. The end plate 420C and the base plate portion 411C may be joined to the first journal 512C and the second journal 522C, respectively, and thus orbital motion of the crank shaft 520C may be converted into rotary motion of each of the end plate 420C and the base plate portion 411C about the output axis OPX. An orbital phase difference between the oscillating gears 610C and 620C may be determined by a difference in eccentricity direction between the first eccentric portion 523C and the second eccentric portion 524C.

When the carrier 400C is fixed, since the oscillating gears 610C and 620C may be meshed with the plurality of internal tooth pins 320 of the outer cylinder 300, oscillating rotation of the oscillating gears 610C and 620C may be converted into rotary motion of the outer cylinder 300 about the output axis OPX.

The input gear 730C may extend along the output axis OPX through a support wall 742. A though hole 525 extending along the output axis OPX may be formed through the crank shaft 520C. A tip end portion of the input gear 730C may be inserted into the through hole 525.

A key groove 732 may be formed at the tip end portion of the input gear 730C. Another key groove 526 may be formed on an inner wall surface of the crank shaft 520C, which forms the through hole 525. The key grooves 732 and 526 may extend substantially parallel to the output axis OPX. A key 733 may be inserted into the key grooves 732 and 526. As a result, the input gear 730C may be joined to the crank shaft 520C, When the input gear 730C rotates about the output axis OPX, the crank shaft 520C may rotate about the output axis OPX. As a result, oscillating rotation of the oscillating gears 610C and 620C may be caused.

The central through hole 417C formed through the base plate portion 411C may include a first hollow portion 491 and a second hollow portion 492. The first hollow portion 491 and the second hollow portion 492 both may have a circular cross section. The first hollow portion 491 may be smaller in cross section than the second hollow portion 492.

In the first hollow portion 491, the second journal 522C and the journal bearing 532C may be disposed. On the other hand, in the second hollow portion 492, the sensor 105 may be disposed. Accordingly, the second hollow portion 492 may be used as a detection space for the sensor 105 to detect a foreign substance. The outer surface 416C of the base plate portion 411C may be brought into pressure-contact with a counterpart member (not shown). Accordingly, a lubricant in the central through hole 417C may be enclosed in the gear device 200C. The detection portion 110A (see FIG. 2A and FIG. 2B) of the sensor 105 may be disposed so as to make contact with the lubricant in the central through hole 417C. It may also be possible that the output portion 120 and the power source 130 are mounted to the counterpart member. In this embodiment, the central through hole 417C may be an example of the through hole.

The second hollow portion 492 may be provided adjacently to the crank shaft assembly 500C. Accordingly, when a large metal piece is generated from the crank shaft assembly 500C, the detection portion 110A can capture the large metal piece generated from the crank shaft assembly 500C.

In this embodiment, it may be preferable that, while the carrier 400C is fixed, the outer cylinder 300 is rotated about the output axis OPX. In this case, electrical connection from the detection portion 110A to the output portion 120 and to power source 130 may be facilitated.

It may also be possible that, in accordance with the design principle described in relation to the third embodiment, the sensor 100A (see FIG. 2A and FIG. 2B) is additionally disposed to detect a foreign substance in a detection space 750 surrounded by the outer wall 740. It may also be possible that, in accordance with a principle described in relation to the sixth embodiment, a designer additionally disposes the sensor 100A in a through hole formed through the outer cylinder 300.

The design principles described in relation to the above-mentioned various embodiments may be applicable to various types of sensors and/or gear devices. It may also be possible that a part of various features described in relation to any one of the above-mentioned various embodiments is applied to the sensor and/or the gear device described in relation to another one of the above-mentioned various embodiments.

The sensors and the gear devices described in relation to the above-mentioned embodiments may mainly have the following features.

A sensor according to one aspect of the above-mentioned embodiments may be provided with a detection portion that detects a foreign substance of a predetermined size or larger generated in a lubricant in a gear device and an output portion that, upon the detection portion detecting the foreign substance, outputs information indicating that the foreign substance has been detected.

A foreign substance of a predetermined size or larger generated in a lubricant in the gear device can cause breakage of various components of the gear device. In addition, in some cases, generation of a large foreign substance may signify a significant decrease in strength of a foreign substance generation source. According to the above-described configuration, upon the detection portion detecting a foreign substance of a predetermined size or larger generated in a lubricant in the gear device, the output portion may output information indicating that the foreign substance has been detected, and thus the sensor can provide notification that a large foreign substance that sharply increases a malfunction risk of the gear device has been generated.

With regard to the above-described configuration, it may also be possible that the detection portion captures the foreign substance.

According to the above-described configuration, the detection portion may capture a foreign substance, and thus the sensor may facilitate analysis of a breakage part of the gear device.

With regard to the above-described configuration, it may also be possible that the sensor is provided further with a power source that supplies electric power to the output portion, a first line that electrically connects the power source to the detection portion, a second line that electrically connects the power source to the output portion, and a third line that electrically connects the detection portion to the output portion. It may also be possible that the foreign substance captured by the detection portion electrically connects the first line to the third line. It may also be possible that under electrical connection between the first line and the third line, the output portion outputs the information by using the electric power supplied from the power source.

According to the above-described configuration, a foreign substance captured by the detection portion may electrically connect the first line to the third line, and under electrical connection between the first line and the third line, the output portion may output information by using electric power supplied from the power source, and thus provided that a circuit continuous from the power source is energized, the sensor can provide notification that a large foreign substance has been detected.

A gear device according to another aspect of the above-mentioned embodiments is provided with an outer cylinder having an inner circumferential surface on which a plurality of internal teeth surrounding a predetermined output axis are formed, an oscillating gear meshed with the plurality of internal teeth, a crank shaft assembly that imparts oscillating rotation to the oscillating gear so that a center of the oscillating gear orbits about the output axis, a carrier that supports the crank shaft assembly and relatively rotates about the output axis with respect to the outer cylinder, and a sensor having a detection portion that detects a foreign substance of a predetermined size or larger floating in a lubricant in a detection space having a boundary at least partially formed by at least one of the outer cylinder and the carrier and an output portion that, upon the detection portion detecting the foreign substance, outputs information indicating that the foreign substance has been detected.

According to the above-described configuration, upon the detection portion detecting a foreign substance of a predetermined size or larger floating in a lubricant in a detection space having a boundary at least partially formed by at least one of the outer cylinder and the carrier, the output portion may output information indicating that the foreign substance has been detected, and thus by the sensor, there is provided notification that a large foreign substance that sharply increases a malfunction risk has been generated.

With regard to the above-described configuration, it may also be possible that the gear device is provided further with an input gear that extends along the output axis and an outer wall having a joint wall that surrounds the input gear and is joined to the outer cylinder and a support wall that supports the input gear. It may also be possible that the carrier includes a first end wall that is opposed to the support wall. It may also be possible that, in cooperation with the outer wall, the first end wall forms the detection space.

According to the above-described configuration, in cooperation with the outer wall, the first end wall may form the detection space, and thus a designer can design the outer wall so that a sufficient space for disposing the sensor in the detection space is formed.

With regard to the above-described configuration, it may also be possible that the sensor is mounted to the outer wall.

According to the above-described configuration, the sensor may be mounted to the outer wall, and thus a designer can easily dispose the sensor without causing interference between the sensor and a movable part of the gear device.

With regard to the above-described configuration, it may also be possible that the detection space is a through bore that extends along the output axis through the carrier and the oscillating gear.

According to the above-described configuration, the detection space may be a through bore that extends along the output axis through the carrier and the oscillating gear, and thus the sensor can easily detect a large peeled-off piece peeled off from the oscillating gear and the carrier.

With regard to the above-described configuration, it may also be possible that the outer cylinder includes an outer circumferential surface that surrounds the inner circumferential surface. It may also be possible that the sensor is fitted into a through bore extending between the inner circumferential surface and the outer circumferential surface.

According to the above-described configuration, the sensor may be fitted into the through bore extending between the inner circumferential surface and the outer circumferential surface of the outer cylinder, and thus the sensor can easily detect a large foreign substance in a lubricant flowing in a direction away from the output axis due to rotation of the outer cylinder or the carrier.

With regard to the above-described configuration, it may also be possible that, while the outer cylinder is fixed, the carrier rotates about the output axis.

According to the above-described configuration, the outer cylinder is fixed, and thus the sensor may be easily disposed in the detection space.

With regard to the above-described configuration, it may also be possible that the crank shaft assembly includes a first journal that rotates about a transmission axis extending parallel to the output axis at a position away from the output axis, a second journal that extends along the transmission axis on an opposite side to the first journal, and a crank shaft that is joined to the oscillating gear between the first journal and the second journal and has an eccentric portion that eccentrically rotates with respect to the transmission axis. It may also be possible that the carrier includes a first end wall to which the first journal is joined and a second end wall to which the second journal is joined. It may also be possible that a through bore into which the second journal is partially inserted is formed through the second end wall. It may also be possible that the through bore is used as the detection space.

According to the above-described configuration, the first journal and the second journal may be joined to the first end wall and the second end wall of the carrier, respectively, and thus the crank shaft may be appropriately supported by the carrier. The eccentric portion joined to the oscillating gear between the first journal and the second journal may eccentrically rotate with respect to the transmission axis, and thus the crank shaft can impart oscillating rotation to the oscillating gear. The through bore formed through the second end wall may be used as the detection space, and thus the sensor can easily detect a large foreign substance generated from the crank shaft assembly.

With regard to the above-described configuration, it may also be possible that the crank shaft assembly includes a first journal that rotates about the output axis, a second journal that, on an opposite side to the first journal, extends along the output axis, and a crank shaft that is joined to the oscillating gear between the first journal and the second journal and has an eccentric portion that performs eccentric rotation with respect to the output axis. It may also be possible that the carrier includes a first end wall to which the first journal is joined and a second end wall to which the second journal is joined. It may also be possible that a through bore into which the second journal is partially inserted is formed through the second end wall. It may also be possible that the through bore is used as the detection space.

According to the above-described configuration, the first journal and the second journal are joined to the first end wall and the second end wall of the carrier, respectively, and thus the crank shaft may be appropriately supported by the carrier. The eccentric portion joined to the oscillating gear between the first journal and the second journal may perform eccentric rotation with respect to the output axis, and thus the crank shaft can impart oscillating rotation to the oscillating gear. The through bore formed through the second end wall may be used as the detection space, and thus the sensor can easily detect a large foreign substance generated from the crank shaft assembly.

With regard to the above-described configuration, it may also be possible that, while the carrier is fixed, the outer cylinder rotates about the output axis.

According to the above-described configuration, the carrier is fixed, and thus the sensor may be easily disposed in the detection space.

INDUSTRIAL APPLICABILITY

The principles of the above-mentioned embodiments may be favorably used for various types of sensors and gear devices.

What is claimed is:

1. A gear device, comprising:
   an outer cylinder having an inner circumferential surface on which a plurality of internal teeth surrounding a predetermined output axis are formed;
   an oscillating gear meshed with the plurality of internal teeth;
   a crank shaft assembly configured to impart oscillating rotation to the oscillating gear so that a center of the oscillating gear orbits about the output axis;
   a carrier configured to support the crank shaft assembly and relatively rotate about the output axis with respect to the outer cylinder; and
   a sensor including:
      a detection portion configured to detect a foreign substance floating in a lubricant in a detection space having a boundary at least partially formed by at least one of the outer cylinder and the carrier; and
      an output portion configured to, upon the detection portion detecting the foreign substance, output information indicating that the foreign substance has been detected.

2. The gear device according to claim 1, further comprising:
   an input gear extending along the output axis; and
   an outer wall including:
      a joint wall surrounding the input gear and joined to the outer cylinder; and a support wall configured to support the input gear,
wherein the carrier includes a first end wall opposed to the support wall, and
wherein the first end wall forms the detection space in cooperation with the outer wall.

3. The gear device according to claim 2, wherein the sensor is mounted to the outer wall.

4. The gear device according to claim 2, wherein the detection space is a through bore extending along the output axis through the carrier and the oscillating gear.

5. The gear device according to claim 2, wherein the outer cylinder includes an outer circumferential surface surrounding the inner circumferential surface, and
wherein the sensor is fitted into a through bore extending between the inner circumferential surface and the outer circumferential surface.

6. The gear device according to claim 2, wherein the outer cylinder is fixed, and the carrier is configured to rotate about the output axis.

7. The gear device according to claim 1, wherein the crank shaft assembly includes:
a first journal configured to rotate about a transmission axis extending parallel to the output axis at a position away from the output axis;
a second journal extending along the transmission axis on an opposite side to the first journal; and
a crank shaft joined to the oscillating gear between the first journal and the second journal, the crank shaft having an eccentric portion configured to rotate eccentrically with respect to the transmission axis,
wherein the carrier includes a first end wall having the first journal joined thereto and a second end wall having the second journal joined thereto,
wherein a through bore having the second journal partially inserted therein is formed through the second end wall, and
wherein the through bore is used as the detection space.

8. The gear device according to claim 7, wherein the carrier is fixed, and the outer cylinder is configured to rotate about the output axis.

9. The gear device according to claim 1, wherein the crank shaft assembly includes:
a first journal configured to rotate about the output axis;
a second journal extending along the output axis on an opposite side to the first journal; and
a crank shaft joined to the oscillating gear between the first journal and the second journal, the crank shaft having an eccentric portion configured to rotate eccentrically with respect to the output axis,
wherein the carrier includes a first end wall having the first journal joined thereto and a second end wall having the second journal joined thereto,
wherein a through bore having the second journal partially inserted therein is formed through the second end wall, and
wherein the through bore is used as the detection space.

* * * * *